(12) United States Patent
Kislov et al.

(10) Patent No.: US 6,996,428 B2
(45) Date of Patent: Feb. 7, 2006

(54) BIOLOGICAL SIGNAL SENSOR AND DEVICE FOR RECORDING BIOLOGICAL SIGNALS INCORPORATING THE SAID SENSOR

(75) Inventors: Alexander V. Kislov, St. Petersburg (RU); Igor A. Novikov, St. Petersburg (RU); Sergey V. Petrovykh, St. Petersburg (RU); Oleg N. Khomyakov, St. Petersburg (RU)

(73) Assignee: Gen3 Partners, Inc., Boston, MA (US)

( * ) Notice: Subject to any disclaimer, the term of this patent is extended or adjusted under 35 U.S.C. 154(b) by 0 days.

(21) Appl. No.: 10/782,542

(22) Filed: Feb. 18, 2004

(65) Prior Publication Data

US 2004/0181141 A1    Sep. 16, 2004

Related U.S. Application Data

(63) Continuation of application No. PCT/US02/27021, filed on Aug. 23, 2002.

(60) Provisional application No. 60/314,950, filed on Aug. 24, 2001, provisional application No. 60/314,925, filed on Aug. 24, 2001.

(51) Int. Cl.
*A61B 5/04* (2006.01)
(52) U.S. Cl. ........................ 600/393; 600/506; 600/547
(58) Field of Classification Search ................ 600/372, 600/386, 393, 506, 547
See application file for complete search history.

(56) References Cited

U.S. PATENT DOCUMENTS

| 3,608,543 | A |   | 9/1971  | Longini |
|-----------|---|---|---------|---------|
| 3,750,649 | A |   | 8/1973  | Severinghaus |
| 3,848,582 | A | * | 11/1974 | Milani et al. ................ 600/372 |
| 4,324,257 | A | * | 4/1982  | Albarda et al. ............. 600/357 |
| 4,448,199 | A |   | 5/1984  | Schmid |
| 5,353,802 | A |   | 10/1994 | Ollmar |
| 6,091,977 | A | * | 7/2000  | Tarjan et al. ................ 600/372 |

* cited by examiner

*Primary Examiner*—Lee S. Cohen
(74) *Attorney, Agent, or Firm*—Kirkpatrick & Lockhart Nicholson Graham LLP

(57) ABSTRACT

The sensor has four electrodes arranged on a common base, three of which are made as closed circuits, placed one into another, whereas the fourth electrode is placed inside the smallest circuit. The external and the central electrodes form a pair of current-feeding electrodes, whereas the electrodes disposed between them form a pair of measuring electrodes. The second design option of the sensor has three electrodes, two of which are made as closed circuits placed one into another, whereas the third electrode is placed inside the electrode that is smaller. The external and the central electrodes form a pair of current-feeding electrodes, and the electrode arranged between them together with the external or the central electrode form a pair of measuring electrodes. The design of sensors makes it possible to use them in combination with biological signal sensors of non-rheographic modality, for example, pulse wave, temperature. The sensor may be incorporated in wristwatch or bracelet.

14 Claims, 3 Drawing Sheets

BIOLOGICAL SIGNAL SENSOR AND DEVICE FOR RECORDING BIOLOGICAL SIGNALS INCORPORATING THE SAID SENSOR

RELATED APPLICATIONS

This application is a Continuation of PCT/US02/27021 filed on Aug. 23, 2002 which claims priority to provisional application Ser. Nos. 60/314,950 and 60/314,925 both of which were filed on Aug. 24, 2001 and all of which are incorporated herein by reference in their entirety.

FIELD OF THE INVENTION

The present invention relates to the field of medical engineering. More particularly, the invention relates to instruments used to measure and record the impedance of a human body area, pulse wave parameters. A preferred field of application of the invention is the monitoring of such parameters to determine the state of health of a human.

BACKGROUND OF THE INVENTION

A rheograph is an electronic instrument with an electrode sensor incorporated in it. It is used to measure the impedance of an area of biological tissue of the body and is a known device for studying physiological indexes of a human organism. In a general case, the sensor's electrodes may be electrically connected with each other and with outside instruments through various schemes of connections. An electrode connection through a conventional tetrapolar scheme is a preferred option. It is customary to use four metal electrodes two of which, named current-feeding electrodes or current-flow electrodes, serve to supply the measuring electric current to a monitored body area, while two other electrodes, named recording or measuring electrodes, serve to measure a voltage drop developing in the body area checked when the measuring current passes through it. The electrodes of the tetrapolar rheograph are usually made as metal rectangular plates applied onto the skin surface of the body area to be monitored, or as metal tapes attached on a plastic template, which is also applied onto the body area under study.

The disadvantage of the majority of the known tetrapolar rheographs consists in the presence of errors in the measurement of the impedance of biological tissue, caused by the fringe effects in the zone of measuring electrodes.

Another tetrapolar rheograph that is free of the above-described disadvantage employs annular current electrodes with the measuring electrodes placed in them. This design of a four-electrode sensor of the rheograph is the following.

The four-electrode sensor comprises two flat annular electrodes, placed on the skin of a human body area under study. A round measuring electrode is placed inside the ring of each current-feeding electrode. A pair of annular current-feeding electrodes is connected to a high-frequency generator via resistors, and a pair of round measuring electrodes is connected to the same generator via resistors and primary windings of the transformer. Because of such a connection, the round electrodes combine the functions of current-feeding and measuring electrodes, and annular electrodes serve as shielding electrodes. This provides the conditions for the formation of measuring current lines in the "volume" of biological tissue under study without dissipation thereof due to the fringe effects.

One of the limitations of the above-described sensor design is its consisting of two separate elements each of which contains a pair of electrodes arranged on a common base, namely, an annular electrode and a flat round electrode (inside of the former). When placed on a human body, each pair of electrodes is fastened independently, which fact cannot ensure an identity of the "electrode-skin" contacts for each pair that is required to obtain reliable measurement results. Additionally, the spaced-apart electrodes present no means of using them as a basis for making a small-sized and technological design. That is, those specific requirements that practice imposes upon the so-called "elements for biological information pickup" are not satisfied.

Other drawbacks of the above-described sensor are as follows. In some cases of making a decision concerning the functional state of human organism, it is necessary to use additional evidence of physiological indicators of other, non-rheographic modality, for example, temperature, pulse pressure in blood vessels, and so forth. These indicators are of particular interest when they are recorded from the same human body area in which the rheographic study is performed.

SUMMARY OF THE INVENTION

The present invention solves the engineering problem of the development of a high-technology, small-sized, and convenient in service design of the rheographic sensor, and of extending the informative capabilities of the said sensor by making it capable of providing data on non-rheographic modality, the data being locally associated with the obtained rheographic data.

A first embodiment of the sensor comprises four electrodes, arranged on a common base, three of which are made as closed circuits, inserted one into another, whereas the fourth electrode is placed inside a smaller circuit. The external and the central electrodes form a pair of the current-feeding electrodes, whereas two electrodes arranged between them form a pair of the measuring electrodes.

To ensure that the results of measurement of tissue impedance are independent of the sensor orientation on a human body, the sensor's electrodes made as closed circuits may be ring-shaped, placed predominantly concentrically.

To facilitate the installation of the sensor on the body areas characterized by complex surface relief, the base, on which all sensor's electrodes are arranged, is made of a flexible dielectric material, for example, rubber.

To equalize the "electrode—skin" transient resistances and thus to facilitate the balancing conditions of an electrode-connected input amplifier of the tetrapolar rheograph, the measuring electrodes have a roughly equal area, for example, composed of insulated parts electrically connected with each other.

To extend the informative capabilities of the electrode sensor, the central electrode has a hole inside which a sensor of non-rheographic modality, for example, a pulse wave sensor, may be placed on the said base.

Another embodiment of the present invention comprises three electrodes arranged on a common base, two of which are made as closed circuits installed one into another, whereas the third electrode is placed inside a smaller electrode. The external and central electrodes form a pair of the current-feeding electrodes, whereas the electrode located between them and the external or the central electrode form a pair of the measuring electrodes.

In a manner similar to that described above, the second embodiment enables the electrodes shaped as closed circuits to be made as rings arranged predominantly concentrically. Similarly to the first option, the base, on which the electrodes are placed, may be made flexible.

To ensure more extensive functional capabilities, the central electrode of the sensor has a hole, inside which a sensor of the non-rheographic modality, for example, a pulse wave sensor, may be placed on the said base.

Due to the above-indicated combination of indicators, the sensor of a physiological parameter of the non-rheographic modality is spatially combined with the electrode rheographic sensor, thus providing the conditions for obtaining the measurement data of the rheographic and non-rheographic modality from the same human body area.

The embodiments of the inventions also include a device made as a wrist-watch or a bracelet for recording biological signals. In this case a sensor utilizing any of the above-mentioned combinations of features, is placed on the wall of wrist-watch or bracelet case facing human arm.

The embodiment of the recording device as a wrist-watch or bracelet provides means for obtaining data of rheographic and non-rheographic modality from a local wrist area, thus, permitting a prolonged and synchronous monitoring of several physiological parameters, for example, an impedance of biological tissue, pulse wave, surface temperature of the body area under study under conditions that are comfortable for human beings.

DETAILED DESCRIPTION OF THE PREFERRED EMBODIMENTS

The biological signal sensor (first design option) comprises four electrodes, three of which are generally made as closed circuits of any shape, for example, oval or annular. In any case they are placed one into another, and the fourth electrode is placed inside the smallest electrode. The said fourth electrode may be also made as a closed circuit or shaped as a flat plate, for example, round plate.

Figure 1:
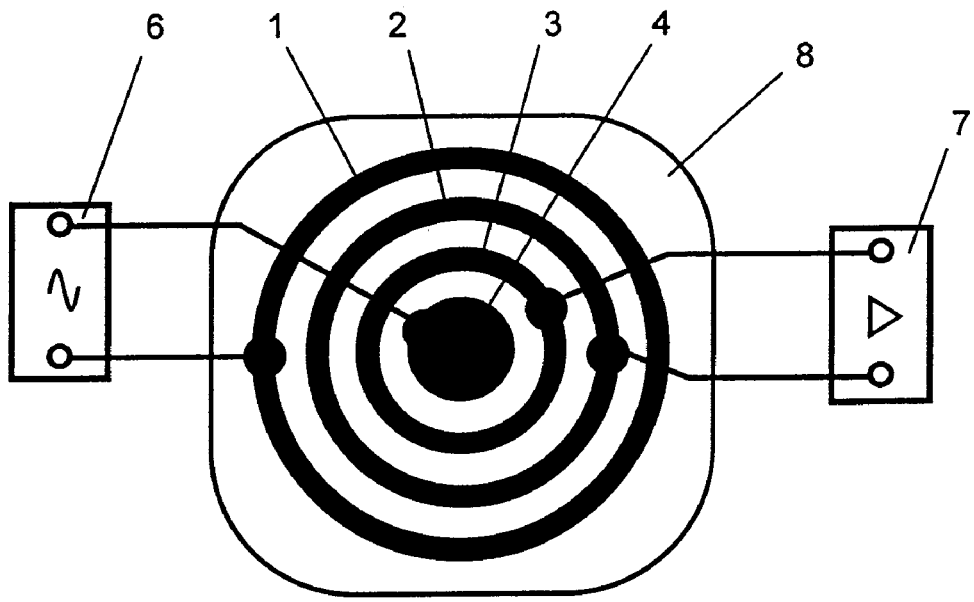
FIG. 1—a four-electrode sensor with three concentric annular electrodes and a round central electrode.
Figure 2:
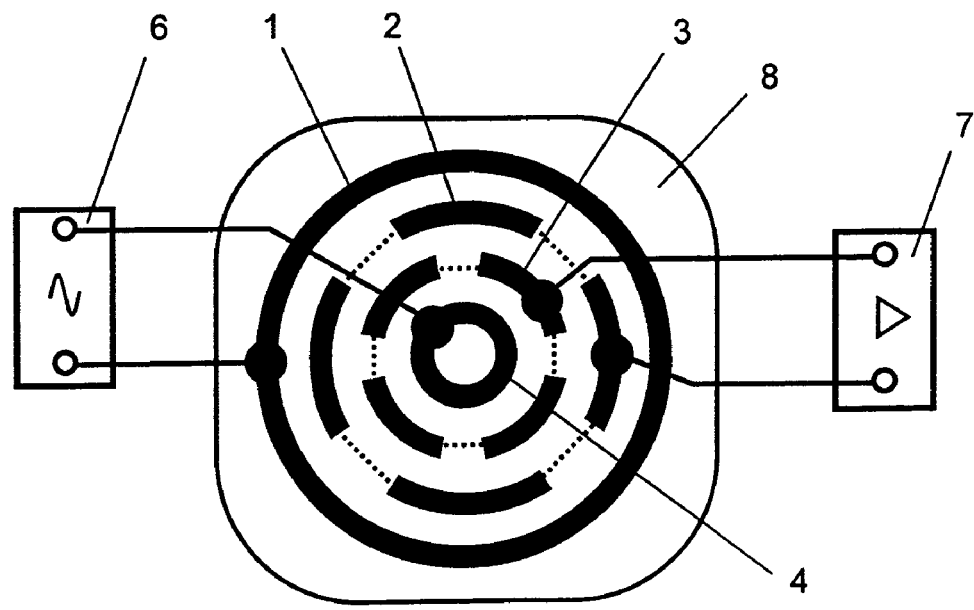
FIG. 2—a four-electrode sensor in which recording electrodes are made of several parts electrically connected with each other.

FIG. 1 shows an embodiment of the sensor connected to the measuring circuit; the sensor has three annular electrodes 1, 2, 3, and central electrode 4 shaped as a round plate. External annular electrode 1 and central round electrode 4 form a pair of current-feeding electrodes, whereas two inner annular electrodes 2 and 3 form a pair of measuring electrodes. Electrodes 1 and 4 are connected to power supply source 6, and electrodes 2 and 3 are connected to recording device 7, for example, to a measuring amplifier. All electrodes 1–4 are arranged on a common base—substrate 8 that may be made of elastic dielectric material, for example, rubber. Because of the annular and round shape of electrodes 1–4, the results of the measurements with the aid of the sensor do not depend on the orientation of the sensor when it is placed on human body area being monitored. The example shows that measuring annular electrodes 2 and 3 have different contact area with the surface of a human body and, hence, different values of the "electrode-skin" transient resistances. This drawback can be eliminated by making electrodes 2 and 3 not as continuous rings but as rings with insulating gaps (FIG. 2), i.e. of insulated parts. And all the conducting parts of each electrode 2 and 3 are electrically connected with each other. The size of the insulating gaps and conducting parts of electrodes 2 and 3 are chosen so that the total area of contact of the conducting parts of electrodes 2 and 3 with skin is the same. This feature of the embodiment of measuring electrodes 2 and 3 facilitates balancing conditions of recording device 7.

Since one of the electrodes of each pair, when in use, is certain to be connected with the case of the entire device, it is made possible to combine these single-potential electrodes in one design. Therefore, the second embodiment of the sensor differs from the first embodiment in that it contains not four, but three electrodes, two of which are generally made as closed circuits of any shape, for example, oval or annular. In any case, they are placed one into another, and the third electrode is placed inside the smallest electrode. Said third electrode may be also made as a closed circuit or have a different shape, for example, shaped as round flat plate.

Figure 3:
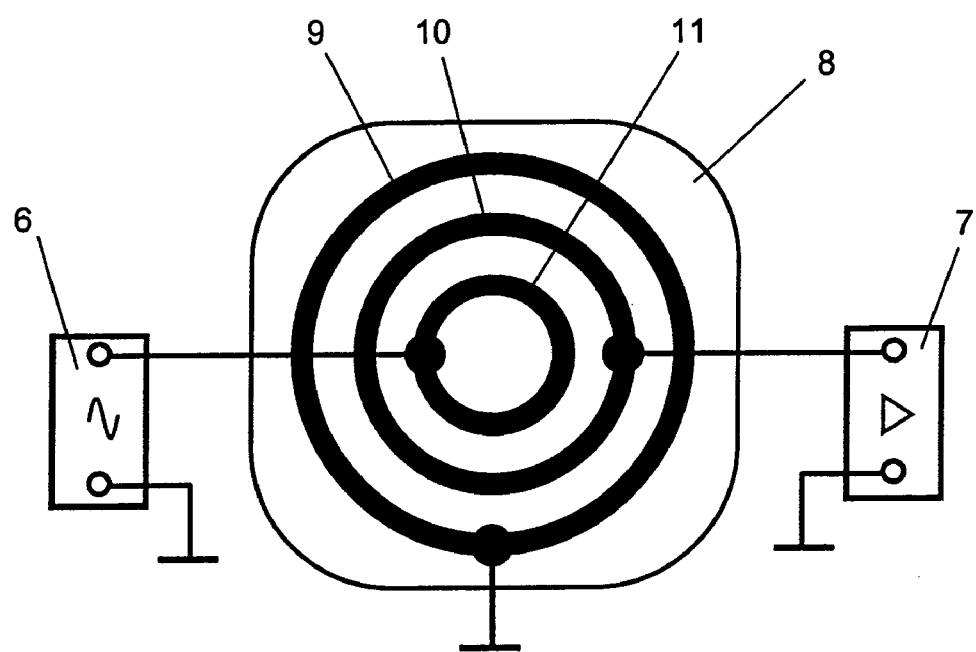
FIG. 3—a three-electrode sensor with concentric annular electrodes.
Figure 4:
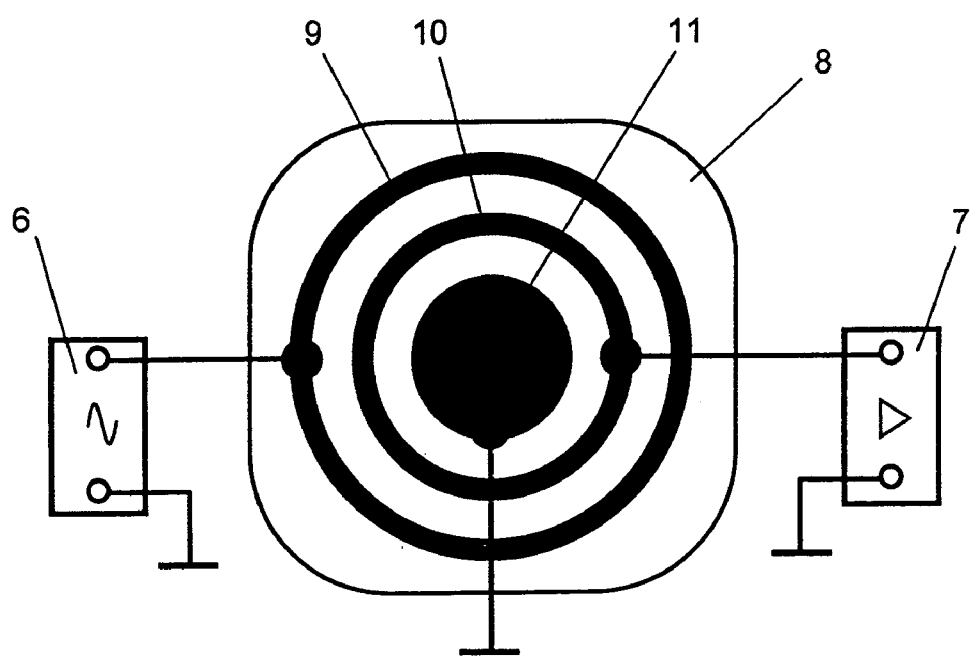
FIG. 4—a three-electrode sensor with a round central electrode.

FIG. 3 and FIG. 4 illustrate different circuit designs of connection of the three-electrode sensor to the power supply source and the measuring circuit.

FIG. 3 provides an example of the embodiment of the sensor with three annular electrodes 9, 10, 11, with said sensor being connected to the measuring circuit. External electrode 9 is grounded and together with central electrode 11 they form a pair of current-feeding electrodes, and together with inner electrode 10 they form a pair of measuring electrodes.

In FIG. 4, central electrode 11 is made as a flat circle, grounded; together with external electrode 9 they form a pair of current-feeding electrodes, and together with inner electrode 10 they form a pair of measuring electrodes.

The use of both embodiments of the sensor gives the same engineering result. If the second embodiment is used, the sensor can be made somewhat smaller in size.

The invention claimed herein (both for the four-electrode and three-electrode rheographic sensor) can be used as a basis for manufacturing a combined sensor to record biological signals of various modality, for example, temperature, arterial pressure, and pulse wave.

Figure 5:
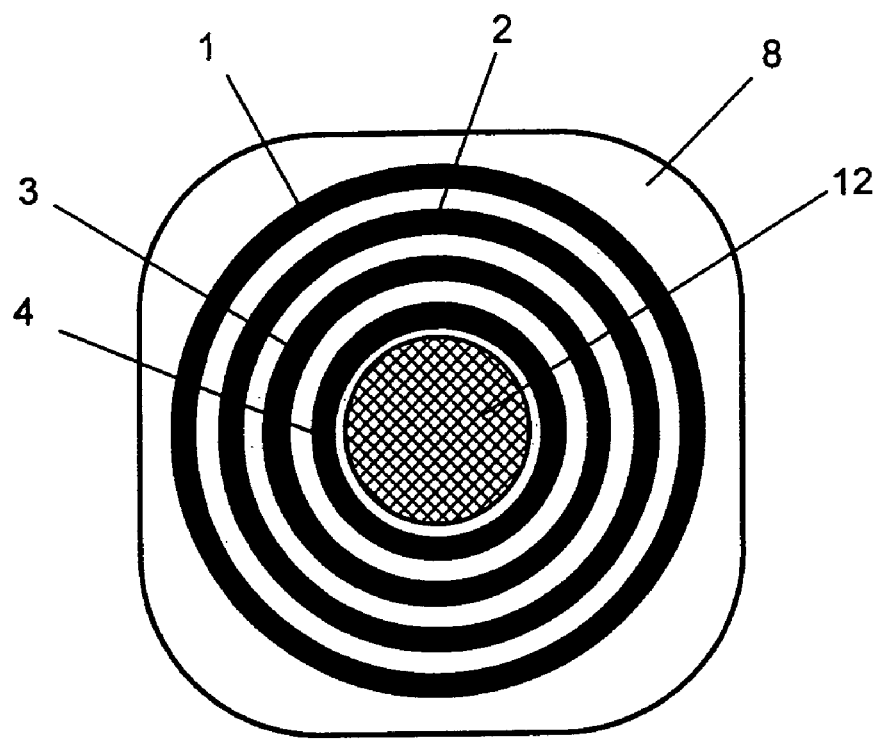
FIG. 5—an example of the embodiment of a combined biological signal sensor on a single base.

In particular, the biological signal sensor shown in FIG. 5 has four concentric annular electrodes 1–4 and pulse wave sensor 12, located inside the electrode that is the smallest; sensor 12 may be made by any known means. For example, it may be made as a strain-measuring or piezoelectric transducer shaped as rectangular or round plate. It may be made as an opto-electronic sensor. In this case, pulse wave sensor 12 is placed together with annular electrodes 1–4 on common base 8, it has a zero potential common to all of them, and permits the pulse wave and the impedance of human body's area to be measured at the same spot on human body.

Figure 6:
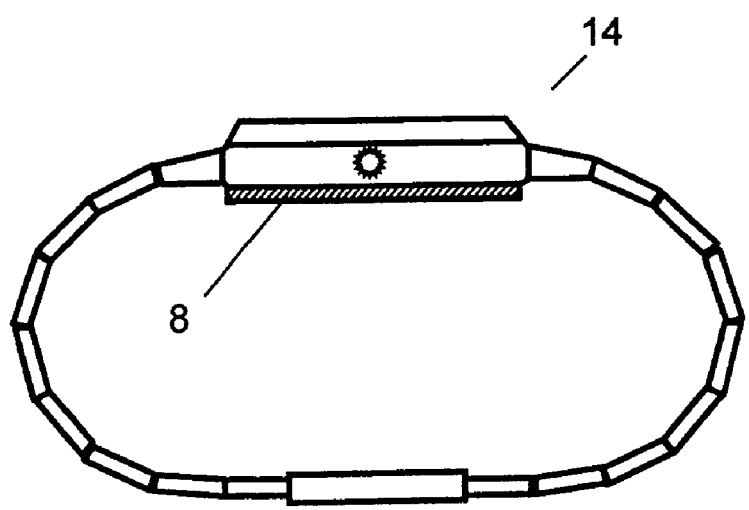
FIG. 6—a wrist-watch with a sensor located in its case.

The sensor intended for recording biological signals (FIG. 6) claimed herein is made as wrist-watch 14 whose case incorporates substrate 8 with any sensor of those described above located on it. The use of a wrist-watch or a bracelet as a carrier for the biological signal sensor permits recording and monitoring of various parameters, recorded in the wrist area and required to estimate human health, while a human being who carries this device may not interrupt his/her routine activity.

What is claimed is:

1. A biological signal sensor comprising:
   a first, a second and a third electrodes disposed on a common base and made as closed circuits and arranged in one another, the first electrode being disposed externally and the third electrode forming a smaller circuit;
   a fourth electrode disposed inside the smaller circuit, the fourth electrode and the first electrode forming a pair of current-feeding electrodes;
   a sensor of non-rheographic modality disposed on the common base inside an opening in the fourth electrode; and
   a pair of measuring electrodes formed by the second and the third electrodes.

2. The sensor of claim 1, wherein the electrodes made as closed circuits are ring shaped.

3. The sensor of claim 2, wherein the ring-shaped electrodes are arranged concentrically.

4. The sensor of claim 1, wherein the common base is made flexible.

5. The sensor of claim 1, wherein the second and third electrodes have about the same area.

6. The sensor of claim 1, wherein the pair of measuring electrodes are made of insulated parts electrically connected with each other.

7. The sensor of claim 1, wherein the sensor of non-rheographic modality comprises a pulse wave sensor.

8. A biological signal sensor comprising:
   a first, a second and a third electrodes disposed on a common base, the first and the second electrode being configured as closed circuits disposed in one another and the first electrode being an external electrode;
   the third electrode being disposed inside the second electrode and forming a pair of current feeding electrodes with the first electrode;
   a sensor of non-rheographic modality disposed on the common base inside an opening in the third electrode; and
   the second electrode forming a pair of measuring electrodes with either the first electrode or the third electrode.

9. The sensor of claim 8, wherein the electrodes made as closed circuits are ring-shaped.

10. The sensor of claim 9, wherein the ring-shaped electrodes are arranged concentrically.

11. The sensor of claim 8, wherein the common base is made flexible.

12. The sensor of claim 8, wherein the sensor of non-rheographic modality comprises a pulse wave sensor.

13. A device for recording biological signals made as a wrist-watch or a bracelet, the device comprising:
   a sensor disposed in a case, the sensor comprising:
      a first, a second and a third electrodes disposed on a common base and made as closed circuits and arranged in one another, the first electrode being disposed externally and the third electrode forming a smaller circuit;
      a fourth electrode disposed inside the smaller circuit, the fourth electrode and the first electrode forming a pair of current-feeding electrodes;
      a sensor of non-rheographic modality disposed on the common base inside an opening in the fourth electrode; and
      a pair of measuring electrodes formed by the second and the third electrodes; wherein the sensor disposed in a case is mounted on a wall intended to face the surface of a patient's arm.

14. A device for recording biological signals made as a wrist-watch or a bracelet, the device comprising:
   a biological sensor disposed in a case, the biological sensor comprising:
      a first, a second and a third electrodes disposed on a common base, the first and the second electrode being configured as closed circuits disposed in one another and the first electrode being an external electrode;
      the third electrode being disposed inside the second electrode and forming a pair of current feeding electrodes with the first electrode;
      a sensor of non-rheographic modality disposed on the common base inside an opening in the third electrode; and
      the second electrode forming a pair of measuring electrodes with either the first electrode or the third electrode;
   wherein the biological sensor is mounted on a wall intended to face the surface of a patient's arm.

* * * * *